US011628448B2

(12) United States Patent
Hraschan

(10) Patent No.: US 11,628,448 B2
(45) Date of Patent: Apr. 18, 2023

(54) METHOD AND APPARATUS FOR THE PRODUCTION OF A ZEOLITE PARTICLE COMPOSITION

(71) Applicant: Jakob Hraschan, Drobollach am Faaker See (AT)

(72) Inventor: Jakob Hraschan, Drobollach am Faaker See (AT)

( * ) Notice: Subject to any disclaimer, the term of this patent is extended or adjusted under 35 U.S.C. 154(b) by 980 days.

(21) Appl. No.: 16/465,704

(22) PCT Filed: Dec. 1, 2017

(86) PCT No.: PCT/EP2017/081223
§ 371 (c)(1),
(2) Date: May 31, 2019

(87) PCT Pub. No.: WO2018/100178
PCT Pub. Date: Jun. 7, 2018

(65) Prior Publication Data
US 2019/0329265 A1    Oct. 31, 2019

(30) Foreign Application Priority Data

Dec. 2, 2016    (EP) ..................... 16202000

(51) Int. Cl.
| | | |
|---|---|---|
| *B01J 29/06* | (2006.01) | |
| *B02C 19/06* | (2006.01) | |
| *A23K 20/28* | (2016.01) | |
| *A23L 33/16* | (2016.01) | |
| *A61K 9/14* | (2006.01) | |
| *A61K 35/02* | (2015.01) | |
| *C01B 39/02* | (2006.01) | |
| *B01J 20/16* | (2006.01) | |
| *B01J 29/70* | (2006.01) | |
| *B01J 37/00* | (2006.01) | |
| *B01J 37/14* | (2006.01) | |
| *B01J 20/28* | (2006.01) | |

(52) U.S. Cl.
CPC ............ *B02C 19/061* (2013.01); *A23K 20/28* (2016.05); *A23L 33/16* (2016.08); *A61K 9/14* (2013.01); *A61K 35/02* (2013.01); *B01J 20/165* (2013.01); *B01J 20/28002* (2013.01); *B01J 20/28004* (2013.01); *B01J 29/70* (2013.01); *B01J 37/0036* (2013.01); *B01J 37/0063* (2013.01); *B01J 37/14* (2013.01); *C01B 39/026* (2013.01); *A23V 2002/00* (2013.01); *B01J 2229/30* (2013.01); *C01P 2004/03* (2013.01)

(58) Field of Classification Search
CPC ........ B01J 2229/30; B01J 29/70; B01J 37/14; B01J 37/0036; B01J 37/0063; B01J 20/165; B01J 20/28002; B01J 20/28004; B07B 7/083; A61K 9/14; A61K 35/02; C01B 39/026; A23V 2002/00; A23L 33/16; A23K 20/28; B02C 19/061; C01P 2002/70; C01P 2004/03
USPC .................................................. 502/60, 407
See application file for complete search history.

(56) References Cited

U.S. PATENT DOCUMENTS

| | | | |
|---|---|---|---|
| 4,522,342 | A | 6/1985 | Muschenborn et al. |
| 4,880,169 | A | 11/1989 | Zander et al. |
| 2009/0226492 | A1 | 9/2009 | Danz et al. |
| 2013/0119174 | A1 | 5/2013 | Lelas et al. |

FOREIGN PATENT DOCUMENTS

| | | | |
|---|---|---|---|
| CN | 105478212 | A | 4/2016 |
| DE | 19755921 | A1 | 6/1999 |
| DE | 10200688 | A1 | 7/2003 |
| DE | 102005053090 | A1 | 5/2007 |
| EP | 0276742 | A2 | 8/1988 |
| HR | P990263 | A2 | 4/2009 |
| WO | 00/64586 | | 11/2000 |
| WO | 2009/133413 | A1 | 11/2009 |
| WO | 2011/007794 | A1 | 1/2011 |
| WO | 2012/017402 | A2 | 2/2012 |
| WO | 2013/098049 | A1 | 7/2013 |

OTHER PUBLICATIONS

Machine Translation of DE 10200688, Jul. 2003.*
Akyuz, T., Strontium and Cesium Sorption of Some Anatolian Zeolites, Journal of Inclusion Phenomena and Molecular Recognition in Chemistry, 1996, 89-91, 26, Kluwer Academic Publishers, Netherlands.
Apostol, L.C. et al., Application of Natural Materials as Sorbents for Persistent Organic Pollutants, Environmental Engineering and Management Journal, 2009, 243-252, 8(2).
Colella, C., Ion Exchange Equilibria in Zeolite Minerals, Mineralium Deposita, 1996, 554-562, 31, Springer-Verlag.
Concepcion-Rosabal, B. et al., Development and Featuring of the Zeolitic Active Principle 2: A Glucose Adsorbent, Zeolites, 1997, 47-50, 19, Elsevier Science Ltd.

(Continued)

*Primary Examiner* — Elizabeth D Wood
(74) *Attorney, Agent, or Firm* — Burns & Levinson, LLP; Daniel W. Clarke

(57) ABSTRACT

The invention provides a method for the production of a zeolite particle composition which has optimized characteristics, such as enhanced adsorption and specific ion exchange properties. A method and an apparatus for producing improved zeolite particle compositions are provided, where the particles are treated with an oxygen-containing gas during micronisation. The zeolite particle compositions can be used in a method for treatment of the human or animal body by therapy and/or prophylaxis, and specifically in a method of treating or preventing conditions of the human or animal body or symptoms of these conditions that are related to heavy metals, endotoxins, exotoxins, and/or bacterial, viral or parasitic intoxications in or of the digestive system, mucosal surfaces or the skin. Also, new zeolite particle compositions can be used as food additive, as filter for purification of water, in packaging materials, or as cosmetic ingredient.

5 Claims, 7 Drawing Sheets

(56) References Cited

OTHER PUBLICATIONS

Concepcion-Rosabal, B. et al., Characterization of Fe2+-containing Natural Clinoptilolite and its Interaction with Sacaccharides, Microporous and Mesoporous Materials, 2000, 161-166, 38, Elsevier Science Ltd.
Dahm, A. et al., Ultra-stable Zeolites—a Tool for In-cell Chemistry, Journal of Biotechnology, 2004, 279-290, 111, Elsevier Science Ltd.
Dakovic, A. et al., Adsorption of Mycotoxins by Organozeolites, Colloids and Surfaces B: Biointerfaces, 2005, 20-25, 16, Elsevier Science Ltd.
Dwyer, M.R. et al., Effects of Inorganic Adsorbents and Cyclopiazonic Acid in Broiler Chickens, Poultry Science 1997, 1141-1149, 76.
Flowers, J.L. et al., Clinical Evidence Supporting the use of an Activated Clinoptilolite Suspension as an Agent to Increase Urinary Excretion of Toxic Heavy Metals, Nutrition and Dietary Supplements, 2009, 11-18, 1, DovePress Journal.
Foo, K.Y. et al., Insights into the Modeling of Adsorption Isotherm Systems, Chemical Engineering Journal, 2010, 2-10, 156, Elsevier Science Ltd.
Grce, M., Antiviral Properties of Clinoptilolite, Microporous and Mesoporous Materials, 2005, 165-169, 79, Elsevier Science Ltd.
Haidouti, C., Inactivation of Mercury in Contaminated Soils Using Natural Zeolites, The Science of the Total Environment, 1997, 105-109, 208, Elsevier Science Ltd.
Herceg, Z. et al., Tribomechanical Micronization and Activation of Whey Protein Concentrale and Zeolite, Sadhana, 2004, 13-26, 29(1), India.
Ikeda, Y. et al., New Insights into the Role of Mitochondrial Dynamics and Autophagy during Oxidative Stress and Aging in the Heart, Oxidative Medicine and Cellular Longevity, 2014, Article ID 210934, 2014, Hindawi Publishing Corporation.
Joshi, J. T., A Review on Micronization Techniques, Journal of Pharmaceutical Science and Technology, 2011, 651-681, 3(7).
Khademinia, S.H. et al., Bismuth Pyromangenate: Hydrothermal and Solid States Synthesis, Characterization and Optical Properties, Journal of Advanced Materials and Processing, 2015, 77-84, 3(1).
Kithome, M. et al., Kinetics of Ammonium Adsorption and Desorption by the Natural Zeolite Clinoptilolite, Soil Science Society of America Journal, 1998, 622-629, 62.
Lim, Y. et al.,Involvement of Protein Kinase C, Phospholipase C. and Protein Tyrosine Kinase Pathways in Oxygen Radical Generation by Asbestos-Stimulated Alveolar Macrophage, Environmental Health Perspectives, 1997, 1325-1327, 105(5).
Liu, J., High-Resolution and Low-Voltage FE-SEM, Imaging and Microanalysis in Materials Characterization, Materials Characterization, 2000, 353-363, 44, Elsevier Science Ltd.
Lowell, S. et al., Characterizations of Porous Solids and Powders: Surface Area, Pore Size and Density, 2004, 1-282, Kluwer Academic Publishers.
Maliou, E. et al., Lead and Cadmium Removal by Ion Exchange, Water Science and Technology, 1992, 133-138, 25(1), Iawprc, GB.
Marsalek, R., Zeta Potential-Applications, 2nd International Conference on Environmental and Industrial Innovation, 2012, 15-19, 35, IACSIT Press, Singapore.
Matsuura, T., et al., Prolonged Antimicrobial Effect of Tissue Conditioners Containing Silver-Zeolite, Journal of Dentistry, 1997, 373-377, 25(5), Elsevier Science Ltd., GB.
Mier, M.V. et al., Heavy Metal Removal with Mexican Clinoptilolite: Multi-Component Ionic Exchange, Water Research, 2001, 373-378, 35(2), Elsevier Science Ltd., GB.
Mizik, P. et al., The Effect of Natural Zeolite on the Excretion and Distribution of Radiocesium in Rats, Abstract: Veterinary Medicine, 1989, 467-74, 34(8). English translation of Abstract included.
Mojzis, J. et al., Preventive Effect of Zeolite in VX Poisoning in Rats: Veterinarni Medicina (Praha), 1994, 443-449, 39(8). English translation of Abstract included.
Mojzis, J. et al., Tissue and Erythrocyte Cholinesterase Inhibition and Protection by Clinoptilolite Pretreatment, Abstract Veterinary and Human Toxicology, 1994, 533-535, 36. Abstract only.
Montezano, A.C. et al., Oxidative Stress and Human Hypertension: Vascular Mechanisms, Biomarkers and Novel Therapies, Canadian Journal of Cardiology, 2015, 631-641, 31(5).
Morishita, M. et al., Pilot Study on the Effect of a Mouthrinse Containing Silver Zeolite on Plaque Formation, Journal of Clinical Dentistry, 1998, 94-96, 9(4). English translation of Abstract only.
Mikawa, T. et al., Antifungal Effect of Zeolite-incorporated Tissue Conditioner Against Candida Albicans Growth and/or Acid Production, Abstract: Journal of Oral Rehabilitation, 1997, 350-357, 24, Blackwell Science Ltd.
Oguz, H. et al., Preventive Efficacy of Clinoptilolite in Broilers During Chronic Aflatoxin (50 and 100ppb) Exposure, Research in Veterinary Science , 2000, 197-201, 69.
Olver, M.D., Effect of Feeding Clinoptilolite (Zeolite) on the Performance of Three Strains of Laying Hens, British Poultry Science, 1997, 220-222, 38(2), Taylor & Francis.
Palubinskaite, D. et al., Influence of Tribomechanical Milling and Activation of Primary Mixtures on the Synthesis of Calcium Silicate Hydrates, Materials Science-Poland, 2006, 395-403, 24(2/1).
Parlat, S.S. et al., Effect of Clinoptilolite on Performance of Japanese Quail (*Coturnix Coturnix japonica*) During Experimental Aflatoxicosis, British Poultry Science, 1999, 495-500, 40, Taylor & Francis.
Pavelic, K. et al., Natural Zeolite Clinoptilolite: New Adjuvant in Anticancer Therapy, Journal of Molecular Medicine, 2001, 708-720, 78, Springer-Verlag.
Pavelic, K. et al., Medical Application of Zeolites, Handbook of Zeolite Science and Technology, 2003, Marcel Dekker, Inc., US.
Poulsen, H.D. et al., Effects of Dietary Inclusion of a Zeolite (Clinoptilolite) on Performance and Protein Metabolism of Young Growing Pigs, Animal Feed Science and Technology, 1995, 297-303, 53, Elsevier Science Ltd.
Ramu, J. et al., Adsorption of Cholera and Heat-Labile *Escherichia coli* Enterotoxins by Various Adsorbents: An In Vitro Study, Journal of Food Protetion, 1997, 358-362, 60(4), International Association of Mil, Food and Environmental Sanitarians, US.
Ricke, S.C. et al., Survival of *Salmonella typhimurium* in Soil and Liquid Microcosms Amended with Clinoptilolite Compounds, Bioresource Technology, 1995, 1-6, 53, Elsevier Science Ltd.
Rivera, A. et al., Characterization and Neutralizing Properties of a Natural Zeolit/Na2CO3 Composite Material, Microporous and Mesoporous Materials, 1998, 51-58, 24, Elsevier Science Ltd.
Rodriguez-Fuentes, G. et al., Antacid Drug Based on Purified Natural Clinoptilolite, Microporous and Mesoporous Materials, 2006, 200-207, 94, Elsevier Science Ltd.
Schwertfeger, K. L. et al., Hyaluronan, Inflammation, and Breast Cancer Progression, Frontiers in Immunology, 2015, 236(6).
Tretyakov, Y.D., Self-Organisation Processes in the Chemistry of Materials, Russian Chemical Reviews, 2003, 651-679, 72(8), Russian Academy of Sciences and Turpion Ltd.
Tserveni-Gousi, A.S. et al., Some Interior Egg Characteristics as Influenced by Addition of Greek Clinoptilolitic Rock in the Hen Diet, Archiv fur Geflugelkunde, 1997, 291-296, 61(6), Verlag Eugen Ulmer GmbH & Co., Stuttgart, Germany.
Wang, P. et al., Natural and Engineered Nano and Colloidal Transport: Role of Zeta Potential in Prediction of Particle Deposition, Langmuir Article, 2009, 6856-6862, 25(12).
Yapar, S. et al., Removal of Phenol by Using Montmorillonite, Clinoptilolite and Hydrotalcite, Adsorption, 2004, 287-298, 10, Kluwer Academic Publishers, Netherlands.

* cited by examiner

FIG. 3 (continuation)
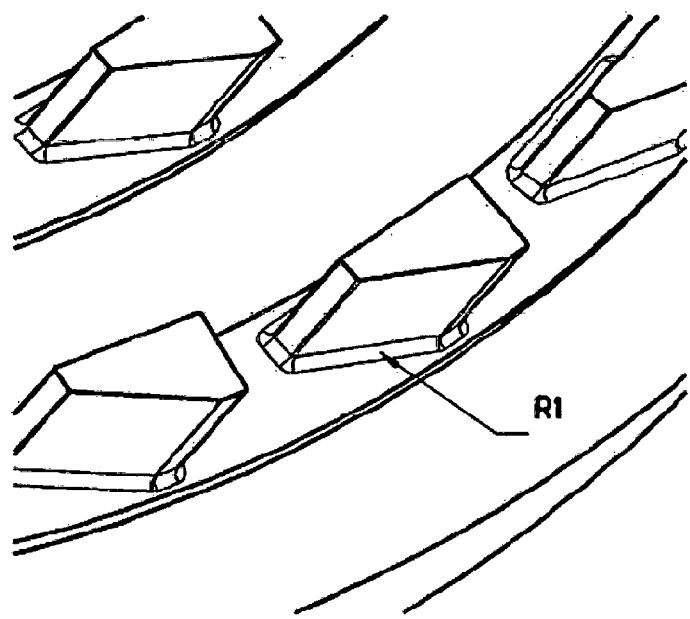
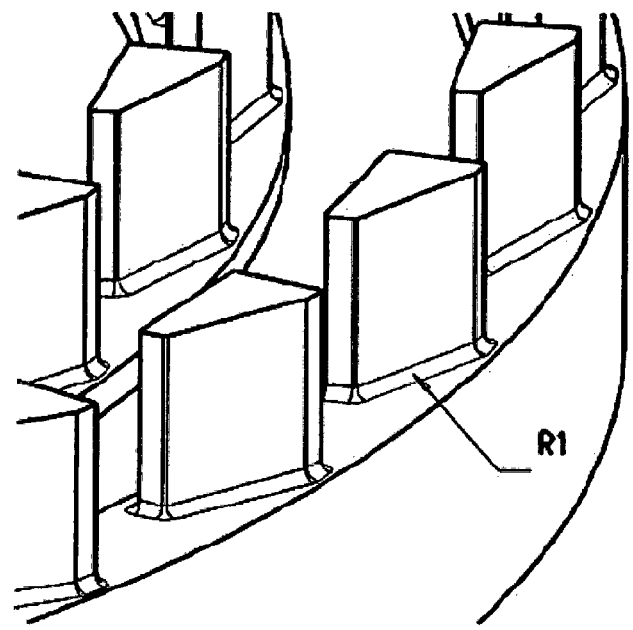

(A)

(B)

(C)

METHOD AND APPARATUS FOR THE PRODUCTION OF A ZEOLITE PARTICLE COMPOSITION

RELATED APPLICATIONS

This application is a national stage application, filed under 35 U.S.C. § 371, of International Application No. PCT/EP2017/081223, filed Dec. 1, 2017, which claims the benefit of priority under 35 U.S.C. § 119(e) to European Application No. 16202000.2, filed Dec. 2, 2016, each of which is incorporated herein by reference in its entirety.

FIELD OF THE INVENTION

This invention relates to new zeolite compositions, a method for the production thereof, an apparatus for producing the compositions, and uses of the compositions.

BACKGROUND OF THE INVENTION

Zeolites are natural hydrated silicates of aluminium and, usually, either sodium or calcium or both. Zeolites have a unique crystal structure of cavities into which small to medium size molecules and cells can be trapped. They exist in natural and synthetic forms and are used extensively as catalysts and adsorbents in many industrial applications. Natural zeolites include heulandite and clinoptilolite.

Zeolites have been used in animal feed to improve animal health and status, as for example described in C. Colella, Mineral Deposita 31:554-562, 1996; M. Kithome, et al., Commun Soil Sci Plant Anal 30:1417-1430, 1999; C. Haidouti, Sci Total Environ 208:105-109, 1997; S. C. Ricke, et al., Bioresource Technology 53:1-6, 1995; H. D. Poulsen and N. Oksbjerg, Animal Feed Science Technology 53:297-303, 1995; J. Mojzis, et al., Vet Human Toxicol 36:533-535, 1994; M. D. Olver, British Poultry Science 38:220-222, 1997.

Further, clinoptilolites are used as food additives for human consumption and as an aid to health, after they are treated with tribo-mechanical action to increase their surface area and destabilize their structure to release their chemical potential, as described in DE 19755921. These materials are thought to be a useful defense against diseases caused directly or indirectly by endo- and exo-toxins, heavy metals, free radicals, neuropathic pain (as described in WO 2013/098049 A1), viruses or bacteria (as described in M. Grce and K. Pavelić, Microporous Mesoporous Materials, 79(1):165-169, 2005).

Natural and synthetic aluminosilicates are materials with adsorption and ion-exchange capacity. They have been extensively used as adsorbents, catalysts, and ion-exchangers in different technical fields, as supplements in animal and human food and beverages, as vehicles to carry low molecular bioactive substances and macromolecules such as proteins into viable cells (as described in A. Dahm and H. Eriksson, Journal of Biotechnology, 111:279-290, 2004), as valuable ingredients of therapeutic compositions in human and veterinary medicine for the treatment of several diseases including cancer, as described in e.g. M. Tomasevic-Canovic, et al., Acta Veterinaria 46:227-234, 1996; H. Oguz, et al., Res Vet Sci 69:89-93, 2000; S. S. Parlat, et al., British Poultry Science 40:495-500, 1999; M. Tomašević-Canovic, et al., Acta Veterinaria 50:23-29, 2000; A. S. Tservenigousi, et al., Archiv fur Geflügelkunde 61:291-296, 1997; M. R. Dwyer, et al., Poultry Science 76:1141-1149, 1997; P. Mizik, et al., Vet Med 34:467-474, 1989; G. Vitorović, et al., Acta Veterinaria 47:159-163, 1997; T. Akyüz, J Inclus Phenom Mol Recogn Chem 26:89-91, 1996; E. Malion, et al., Wat Sci Tech 25:133-138, 1992; T. Uchida, et al., ASAIO Journal 41:221-226, 1995; L. Mavilia, et al., Mat Eng 8:43-47, 1997; H. Nikawa, et al., J Oral Rehabil 24:350-357, 1997; M. Morishita, et al., J Clin Dent 9:94-96, 1998; T. Matsuura, et al., J Dentistry 25:373-377, 1997; J. Mojzis, et al., Veterinarni Medicina 39:443-449, 1994; G. Rodriguez-Fuentes, et al., Zeolites 19:441-448, 1997; J. Ravin, et al., J Food Protection 60:358-362, 1997; A. Rivera, et al., Micropor Mesopor Mat 24:51-58, 1998; B. Concepcion-Rosabal and G. Rodriguez-Fuentes, Zeolites 19:47-50, 1997; B. Concepcion-Rosabal, et al., Micropor Mesopor Mat 38:161-166, 2000; Y. Lim, et al., Environ Health Perspect, 105(suppl 5):1325-1327, 1997; K. Pavelić, et al., J Mol Med 78:708-720, 2001. Also, aluminosilicates have been used for the treatment of disease side-effects such as pain (as described in WO 2011/007794 A1).

The term micronization is generally used to describe a reduction of particle size to less than 10 microns. Size reduction by micronization can for example be achieved by acceleration of particles so that grinding occurs by particle-to-particle impact or impact against a solid surface. In fluid-energy mills (also known as jet mills), micronization is achieved by high impact velocity as a result of particle acceleration in a fast gas stream. In a jet mill, particle velocities are in the range of 300-500 meters per second, compared to 50-150 meters per second in a mechanical impact mill. A description of different micronization processes is given in e.g. J. T. Joshi, Journal of Pharmaceutical Science and Technology, 3(7):651-681, 2011; EP 276 742; U.S. Pat. No. 4,522,342; and HR P990263 A2.

The micronization process provides main advantages, in particular for materials used in the field of medicine, such as increased bioavailability, increased surface area and bioequivalence, as for example described in Z. Herceg et al., Sadhana 29(1):13-26, 2004.

Mechanical processing is used for a number of commercially available zeolite compositions (e.g. Megamin®) and is known to cause a decrease of the particle size of zeolites, changes in the particle size distribution, and an increase of their specific surface area. As the particle size decreases, the structure of the crystal lattice may change. This modifies electron energy levels and electron emission, and other processes may appear. During mechanical processing, solid particles undergo elastic and plastic deformation until the pressure becomes larger than the material can tolerate. This causes the particles to split into much smaller particles and those smaller particles undergo a further dispersion at a certain rate. The consequence is that the mechanical energy is being distributed into elastic and plastic deformations, while new surfaces appear due to breaking of chemical bonds and movement of particles (D. Palubinskaite and A. Kantautas, Materials Science-Poland, 24(2/1), 2006; Y. D. Tretyakov, Russ Chem Rev, 2003, 72:651-679). These procedures of fine grinding and micronization of raw zeolite components under dynamic processing conditions which do not cause chemical changes in the raw materials have become known under the name "tribo-mechanically micronizing" and have been disclosed by the inventors (HR P990263 A2; US 2013/0119174 A1; WO 2000/064586 A1; DE 10200688 A1).

Zeolites have previously been used to remove toxic agents present in a human or animal body, as described in e.g. J. R. Flowers, et al., Nutrition and Dietary Supplements 1:11-18, 2009; M. Vaca Mier, et al., Waters Res 35(2):373-378, 2001; L. C. Apostol and M. Gavrilescu, Enviromental Engineering and Management Journal, 8(2):243-252, 2009; S. Yapar and M. Yilmaz, Adsorption 10:287-298, 2004; and A. Dakovic, et al., Colloids Surf B Biointerfaces, 46:20-25, 2005.

Examples of toxic agents are free radicals. Free radicals are defined as atoms or groups of atoms with an unpaired number of electrons in the outer orbital, which are often formed during oxygen interaction with diverse molecules. The radicals are highly chemically reactive and can damage tissue and cells within the body, including the genome (DNA). The reactions with free radicals occur as a chain reaction and affected cells or tissue may lose their function and die. Free radicals are being linked to diverse diseases such as cardiovascular disease, cancer, and neurodegenerative disease, as well as aging (K. L. Schwertfeger, et al., Front Immunol, 6:236, 2015; A. C. Montezano, et al., Can J Cardiol 31(5):631-641, 2015; Y. Ikeda, et al., Oxid Med Cell Longev 2014:210934, 2014).

The effectiveness and speed of biological action of aluminosilicates is generally described in relation to structural properties such as surface area and ion exchange characteristics. However, no clear correlation between the micronization process, which is also referred to as activation, and the material properties that bring about biological effects has been previously disclosed. Many different approaches and methods for activation or modification of zeolite particles by micronization which differ based on the production methods (US 2013/0119174 A1; WO 2000/064586 A1; DE 10 200 688 A1) or treatment possibilities (WO 2012/017402 A2) have been described in patent applications, but a structure-activity relationship for the materials produced has not been shown.

SUMMARY OF THE INVENTION

It is an object of the invention to provide new zeolite particle compositions which have optimized characteristics. More specifically, it is an object of the invention to provide new zeolite particle compositions which exert enhanced adsorption and specific ion exchange properties. Furthermore, it is an object to provide a method, as well as an apparatus, for producing zeolite particle compositions which have optimized characteristics. Also, it is an object to provide a new zeolite particle composition for use in a method for treatment of the human or animal body by therapy and/or prophylaxis, and specifically in a method of treating or preventing conditions of the human or animal body or symptoms of these conditions that are related to heavy metals, endotoxins, exotoxins, and/or bacterial, viral or parasitic intoxications in or of the digestive system, mucosal surfaces or the skin. Furthermore, it is an object to provide a use of new zeolite particle compositions as food additive, as filter for purification of water, in packaging materials, or as cosmetic ingredient. Finally, it is an object to provide pharmaceutical compositions containing the new zeolite particle compositions.

The invention provides a zeolite particle composition wherein the particles are characterized by
(i) a specific surface area of 30.5 to 30.8 m²/g, wherein the specific surface area is measured by multipoint BET surface area measurement; and
(ii) an average of zeta potential values of less than −12.00 mV, wherein the zeta potential values are measured after addition of $Ni^{2+}$ ions at a concentration of 0.001 M to 50 ml of an aqueous composition containing 50 mg of zeolite particles at different pH values in the pH range of 3.2 to 6.0 where the different pH values are achieved by adding 0.1 M HCl in aliquots of 20 µl to the aqueous composition and wherein the zeta potential values are calculated based upon experimentally-determined electrophoretic mobility.

Also, the invention provides a method for the production of a zeolite particle composition, comprising the steps of
(a) providing natural zeolite particles containing at least 85 wt. % of clinoptilolite as determined by X-ray diffraction and having a volume based particle size as measured by laser diffraction ranging between 0.001 and 0.5 mm;
(b) introducing the particles provided in step (a) in a first micronization device via a particle inlet tube (6) and tribo-mechanically micronizing the particles;
(c) collecting the particles micronized in step (b) at a particle outlet port of the first micronization device;
(d) introducing the particles collected in step (c) in the first or a second micronization device via a particle inlet tube (6) and tribo-mechanically micronizing the particles; and
(e) collecting the particles micronized in step (d) at a particle outlet port of the second micronization device;
(f) optionally repeating steps (d) and (e);
wherein the particles are treated with a gas containing at least 95 mol-% of oxygen throughout at least one of steps (b) or (d).

Furthermore, the invention provides an apparatus for the production of a zeolite particle composition, containing at least one micronization device, wherein the micronization device(s) contain(s)
(a) a particle inlet tube (6);
(b) a gas feed tube (7) connected to the particle inlet tube (6);
(c) a tribo-mechanical micronization unit;
(d) a particle outlet port.

According to a further aspect, the invention provides the zeolite particle composition as described above or as obtained by the above described method for use in a method for treatment of the human or animal body by therapy and/or prophylaxis.

More particularly, the invention provides these zeolite particle compositions for use in a method of treating or preventing conditions of the human or animal body, or symptoms of these conditions that are related to heavy metals, endotoxins, exotoxins, and/or bacterial, viral or parasitic intoxications in or of the digestive system, mucosal surfaces or the skin.

Also, the invention provides the use of the zeolite particle composition as described above or as obtained by the above described method as a food additive, as a filter for purification of water, in packaging materials, or as a cosmetic ingredient.

Finally, the invention provides pharmaceutical compositions containing the above described zeolite particle composition.

DETAILED DESCRIPTION OF THE INVENTION

Zeolite Compositions

Figure 1:
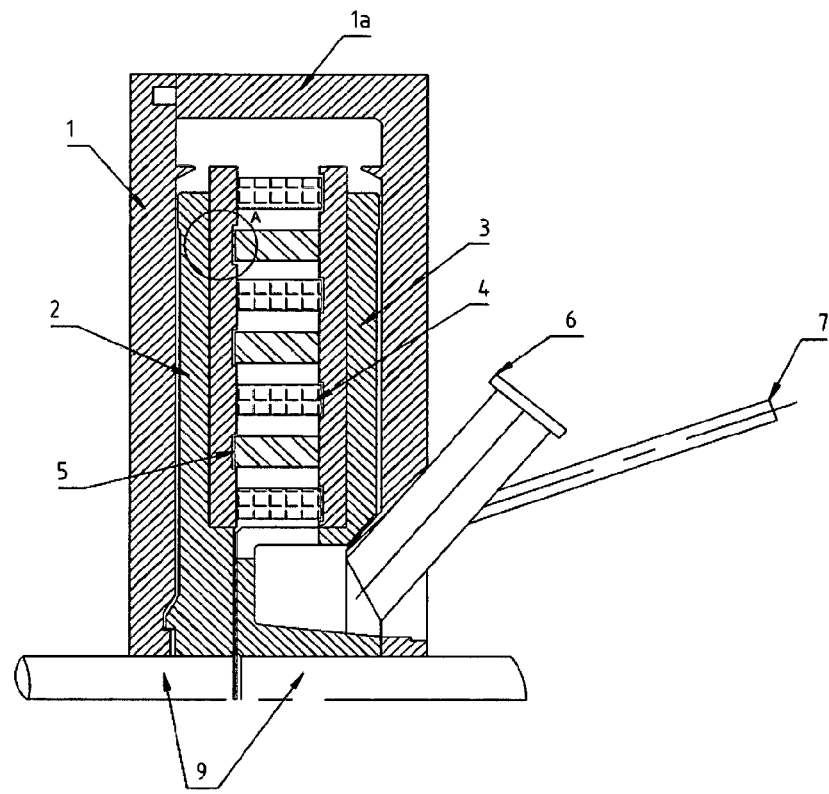
FIG. 1 shows a cross section of the micronisation device used in the method of the invention. The micronisation device contains a stainless steel housing (1, 1*a*), rotor discs (2, 3), circular rows of blades (4, 5), a particle inlet tube (6), a gas feed tube (7), and a shaft (9). "A" indicates the part of the device depicted in FIG. 2.
Figure 2:
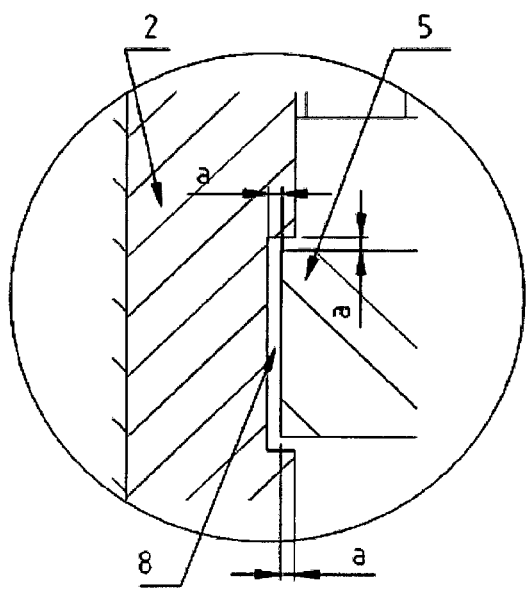
FIG. 2 shows a detail of the cross section of the micronisation device, which shows how the blades (5) protrude into corresponding channels (8) located on the opposing disc (2).
Figure 3:
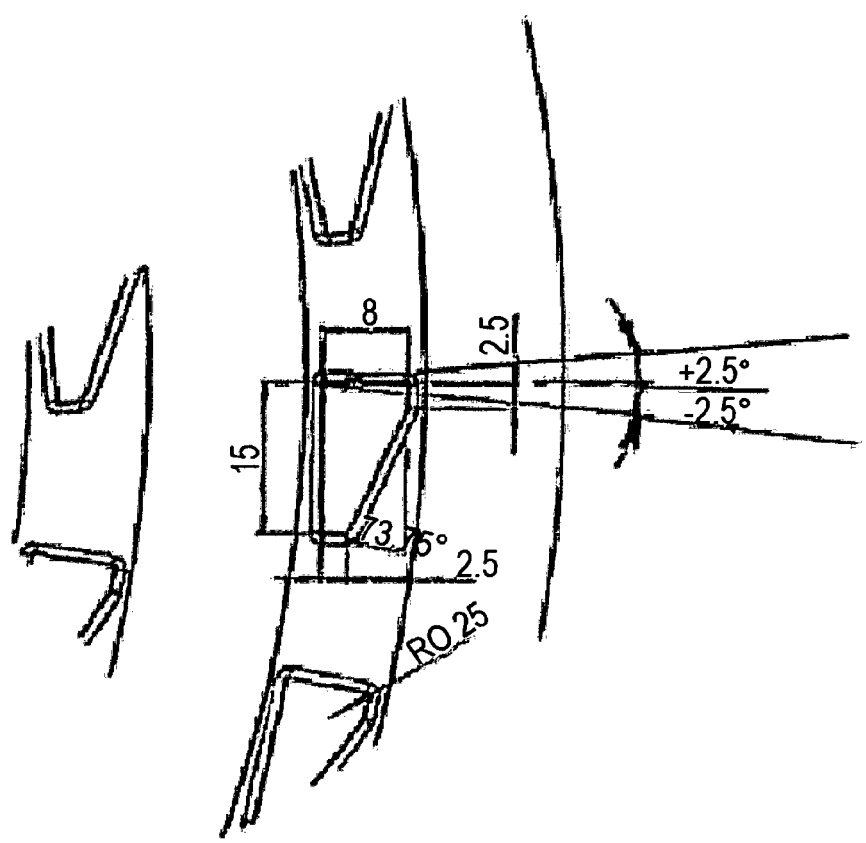
FIG. 3 shows details of the circular rows of blades (4, 5).
Figure 4:
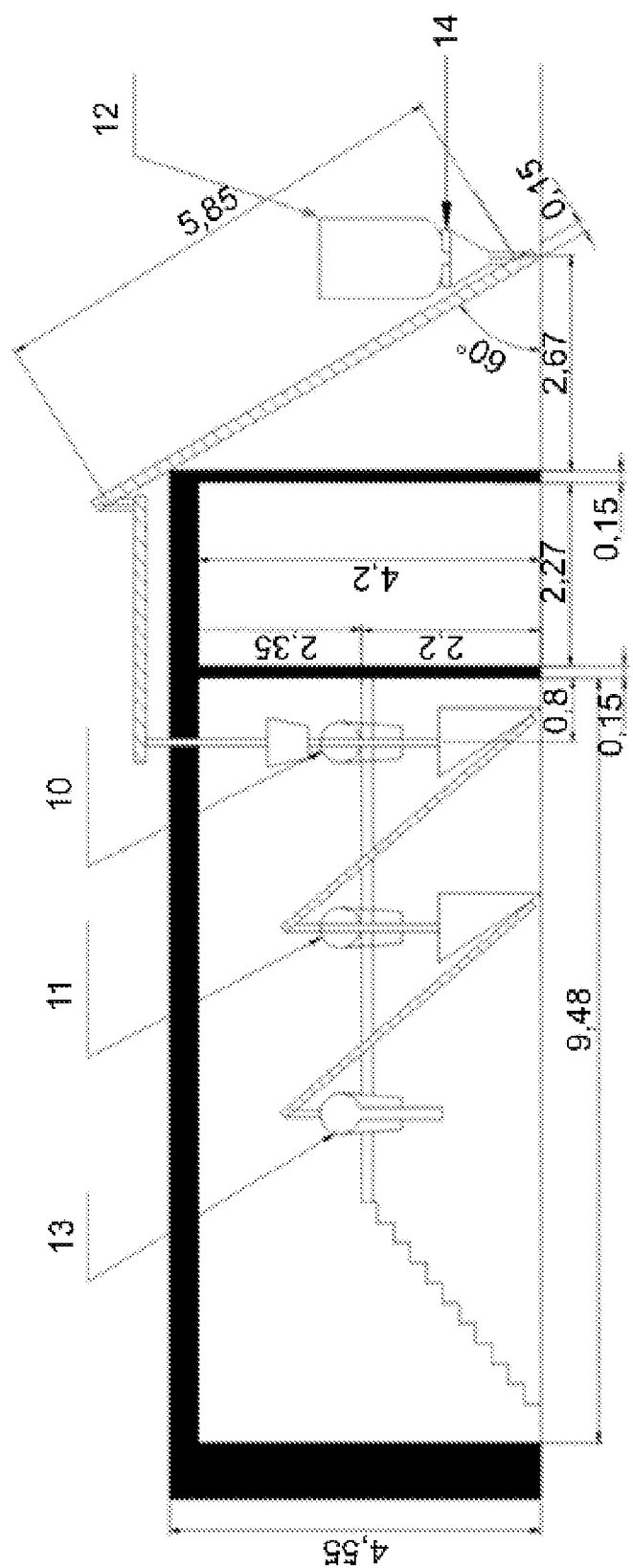
FIG. 4 shows an apparatus containing two micronization devices (10, 11) which are connected through a particle transporting system which connects the outlet port of the first micronization device with the particle inlet tube of the second micronization device. The particles are fed from a Big-Bag emptying unit (12) into the first micronization device. The particles collected from the second micronization device are passed through a flow separator (13). The arrow (14) indicates a sieve with a 3 mm grid.
Figure 5:
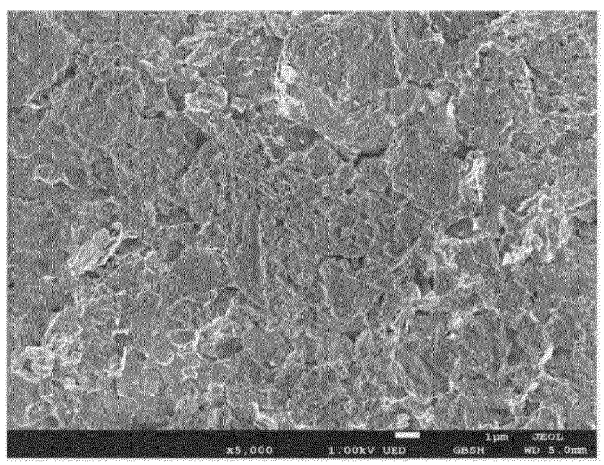
FIG. 5 shows the surface of the zeolite particles of the invention (A) (obtained as described in Example 1), of tribo-mechanically activated zeolite-clionoptilolite (B) (obtained as described in Example 3) and of mechanically micronized (pin mill) natural zeolite clinoptilolite (C) (described in Example 4). The pictures were obtained by SEM analysis.
Figure 5:
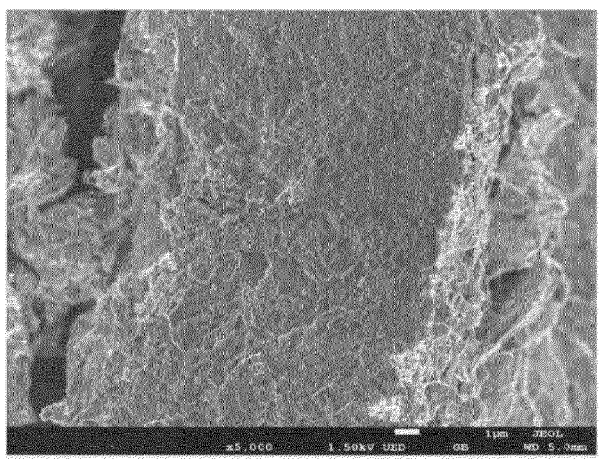
Figure 5:
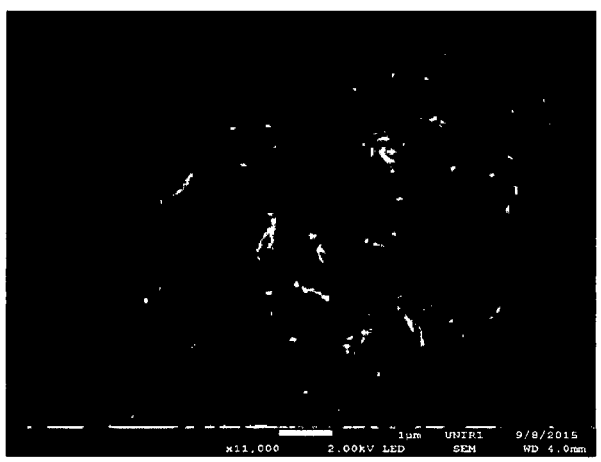

The technical problem this invention aims to solve is providing zeolite compositions which have enhanced adsorption and ion exchange properties. The zeolite compositions can be used in an efficient manner in methods of treating or preventing conditions of the human or animal body, or symptoms of these conditions that are related to heavy metals, endotoxins, exotoxins and/or bacterial, viral or parasitic intoxication in or of the digestive system, mucosal surfaces or the skin.

According to the invention, the zeolite particles are prepared from natural zeolites. Examples of natural zeolites are clinoptilolite, silver zeolite, mordenite, phillipsite and analcite. However, also synthetic zeolites exist, such as Zeolite A, Zeolite W and Zeolite X.

Properties of zeolite compositions which are related to biological effects are their specific surface area, elemental distribution on the surface, ion-exchange properties and zeta potential. To achieve the desired improvement of biological effects, it was found advantageous to increase the surface area, to change the elemental distribution on the surface, to maintain the positive ion-exchange properties and to provide compositions with a negative zeta potential in the acidic pH of the stomach.

The zeolite particle compositions of the invention are characterized by a larger specific surface area in comparison with other mechanically or tribo-mechanically activated zeolites. More particularly, the zeolite particle compositions are characterized by a specific surface area of 30.5 to 30.8 $m^2/g$, wherein the specific surface area is measured by multipoint BET surface area measurement.

The Brunauer-Emmett-Teller (BET) surface analysis technique allows measurement of the precise specific surface area of materials by nitrogen multilayer adsorption. The surface area is measured as a function of relative pressure using a fully automated analyzer. This is a standard physicochemical analytical method for characterization of porous solids and powders. The method evaluates the external area and the pore area of particles to determine the total specific surface area expressed in $m^2/g$. The obtained information is important when studying the effects of surface porosity and particle size in many applications. The surface area depends on factors such as particle size, the presence of cracks or crevasses, surface roughness, and accessible pores. The characteristics of the pores, such as size, volume, and shape can greatly affect the performance of the material (S. Lowell, et al., Characterization of Porous Solids and Powders: Surface Area, Pore Size and Density, Kluwer Academic Publisher, 2004; K. Y. Foo and B. H. Hameed, Chemical Engineering Journal 156: 2-10, 2010).

The specific surface area can for example be determined by nitrogen adsorption/desorption isotherm measurements using a Brunauer-Emmett-Teller (BET) analyzer TriStar II 3020 (Micromeritics, Norcross, Ga., USA). The BET specific surface area, $S_{BET}$, can be calculated using the adsorption branch in the relative pressure range between 0.05 and 0.30.

The zeta potential values of the zeolite particle compositions of the invention show a different pattern upon addition of $Ni^{2+}$ in comparison with other mechanically (ball or pin mill) and/or tribo-mechanically activated zeolites, particularly in an acidic pH range of 3.2 to 6.0. The average of zeta potential values measured after addition of $Ni^{2+}$ ions at a concentration of 0.001 M to 50 ml of an aqueous composition containing 50 mg of zeolite particles at different pH values in the pH range of 3.2 to 6.0 where the different pH values are achieved by adding 0.1 M HCl in aliquots of 20 µl to the aqueous composition and wherein the zeta potential values are calculated based upon experimentally-determined electrophoretic mobility is less than −12.00 mV. This suggests better adsorption capacities for $Ni^{2+}$ ions of the inventive compositions in an acidic pH range, which is particularly relevant when the compositions are present in a human intestine environment having an acidic pH value.

The zeta potential (ζ) can be calculated using theoretical models and an experimentally determined electrophoretic mobility or dynamic electrophoretic mobility. This is a standard method for the assessment of the stability of colloidal dispersions, the character of the particle surface itself and the processes running on the particle surface (e.g. adsorption, ion exchange, modification) (R. Marsalek, Zeta Potential—Applications, 2nd International Conference on Environment and Industrial Innovation, IPCBEE, Vol. 35, 2012; P. Wang, A. A. Keller, Langmuir, 25(12):6856-6862, 2009).

The zeta potential values of an aqueous zeolite particle composition are measured at different pH values as follows:
1. an aqueous zeolite particle composition is prepared by suspending 50 mg of zeolite particles in 50 ml of distilled water in a 100 mL vial on a magnetic stirrer;
2. the pH value of the aqueous composition is measured;
3. where necessary, the pH value is adjusted to 11 with 1.0 M NaOH;
4. 0.1 M HCl solution is added in aliquots of 20 µL to the aqueous composition by titration to gradually decrease the pH of the composition; and
5. immediately after each addition of 20 µl of 0.1 M HCl, the pH of the zeolite particle composition is measured and the zeta potential is measured by placing an aliquot (2.4 mL) of the composition in a plastic cuvette for zeta potential and ion mobility measurement.

For determining the average of the zeta potential values measured after addition of $Ni^{2+}$ ions at different pH values in the pH range of 3.2 to 6.0, the following procedure is used:
1. an aqueous zeolite particle composition is prepared by suspending 50 mg of zeolite particles in 50 ml of distilled water;
2. 0.1 M $Ni^{2+}$ stock solution is added to the aqueous composition to obtain a concentration of 0.001 M $Ni^{2+}$ ions in the composition;
3. the pH of the aqueous composition is measured;
4. where necessary, the pH value is adjusted to 11 with 1.0 M NaOH;
5. 0.1 M HCl is added in aliquots of 20 μl to the aqueous composition to gradually decrease the pH of the composition;
6. after each addition of 20 μl of 0.1 M HCl, the pH of the composition is measured and the zeta potential is measured by placing an aliquot (2.4 mL) of the aqueous composition in a plastic cuvette for zeta potential and ion mobility measurement; and
7. the average of the zeta potential values measured at pH values in the range of 3.2 to 6.0 is calculated.

To determine the point of zero charge and the surface charge density, mass titration measurement of the zeolite particle compositions can be performed in a concentration range from 0 to 20 g/L in NaCl and HCl solution at an ionic strength of 0.0001 mol $dm^{-3}$. The system measurement set-up includes a thermal bath at 25° C., a magnetic stirrer, an ultrasonic probe and a gas inlet for argon. After addition of a small amount of zeolite particle composition in solution, the ultra-sonic probe is applied for one minute. Measurement of the solution pH value is carried out under argon with a glass electrode. The procedure is repeated for NaCl and HCl until the pH value stabilizes and does not change upon addition of a new zeolite particle composition portion.

According to a preferred embodiment, the particles of the zeolite particle composition of the invention are characterized by clear differences in structure in comparison with other mechanically or tribo-mechanically activated zeolites.

More particularly, the particles are preferably further characterized by a silicon to aluminum ratio at the surface of 4.0 to 5.5, wherein the ratio is measured by Energy Dispersive X-ray Diffraction at an accelerating voltage of 15 kV. The ratio of silicon to aluminum in the crystal structure of zeolite particles in the compositions according to the preferred embodiment is different, in that the ratio is in favor of silicon atoms when compared with the ratios in other mechanically and/or tribo-mechanically activated zeolite materials. Preferably, the particles are characterized by a silicon to aluminum ratio at the surface of 4.9.

Furthermore, in addition to the standard crystal flake-like structures and larger surface portions present in other mechanically and/or tribo-mechanically activated zeolites, the compositions according to the invention contain finer (smaller), rounded particles.

The shape and structure of the zeolite particles can be assessed by use of field emission scanning electron microscopy (FE-SEM) in combination with Energy Dispersive X-ray Spectroscopy (EDS; secondary electron images) for the analysis of the elements on the surface. For example, a JSM-7800F FE-SEM instrument (JEOL Ltd., Tokyo) can be combined with an X-MAX80 Aztec EDS (Oxford instruments). To perform such analysis, zeolite particles are put on a sample holder with carbon paste. Accelerating voltages for SEM and EDS are applied at e.g. 2 kV (0.5 kV) and 15 kV, respectively. For EDS measurements, it is suggested to select five different places to estimate reproducibility. This method is widely used in the characterization of materials and provides unambiguous data on the surface properties of materials. The surface properties are correlated with material properties (S. H. Khademiniaa and M. Behzad, Journal of Advanced Materials and Processing, Vol. 3(1), 77-84, 2015; J. Liu, Materials Characterization 44:353-363, 2000).

Furthermore, in a preferred embodiment, the particles of the zeolite particle composition of the invention are characterized by a reduced particle size in comparison with other mechanically and tribo-mechanically activated zeolites.

The particle size of mechanically pre-ground particles (ball mill) could be reduced by a factor of 3 to 4.

The particle size of the zeolite particle compositions can be measured by laser light scattering or diffraction measurements. In such measurements, a group of particles is irradiated with laser light and the particle size distribution is calculated from the light intensity distribution pattern of the scattered or diffracted light emitted from that group of particles.

Measurement of the particle size distribution of zeolite particle compositions can be performed by laser light scattering (diffraction) on a ZetaPlus instrument (Brookhaven). With this instrument, particle sizes in the range 40 nm to 2500 μm can be measured. Powder samples of zeolites can be analyzed as liquid suspensions, without addition of surfactants or other dispersing agents. Ultrasonic dispersion should be applied to the sample before measurement of the particle size distribution to avoid particle aggregation. Colloidal solutions can be prepared by mixing 250 mg of each zeolite particle composition in 250 mL of Milli-Q water to obtain a final concentration of 0.001 g/mL zeolite particles in solution. After dispersion during 5 minutes in an ultrasonic bath, aliquots of 2.4 mL can be placed in plastic cuvettes and the particle size distribution can be assessed.

Method for the Production of a Zeolite Particle Composition

In a further aspect of the invention, a method for the production of zeolite particle compositions is provided. The method of the invention comprises the steps of
(a) providing natural zeolite particles containing at least 85 wt. % of clinoptilolite as determined by X-ray diffraction and having a volume based particle size as measured by laser diffraction ranging between 0.001 and 0.5 mm;
(b) introducing the particles provided in step (a) in a first micronization device via a particle inlet tube (6) and tribo-mechanically micronizing the particles;
(c) collecting the particles micronized in step (b) at a particle outlet port of the first micronization device;
(d) introducing the particles collected in step (c) in the first or a second micronization device via a particle inlet tube (6) and tribo-mechanically micronizing the particles; and
(e) collecting the particles micronized in step (d) at a particle outlet port of the second micronization device;
(f) optionally repeating steps (d) and (e).

The particles are treated with a gas containing at least 95 mol-% of oxygen throughout at least one of steps (b) or (d).

The natural zeolite particles provided in step (a) contain at least 85 wt. % of clinoptilolite. The remaining 15% may consist of other mineral composition, such as cristobalite, biotite and silica.

The mineralogical composition of the zeolite particles can, for example, be as follows:
Clinoptilolite: 86%
Cristobalite: 6%
Biotite: 5%
Silica: 2%
Feldspar: traces
Illite: traces
Carbonate minerals: traces The natural zeolite particles can have a porosity of 32 to 40% and a total exchange capacity of $NH_4$ ranging between 1.2 and 1.5 mol/kg.

The chemical composition of zeolite particles can be determined by atomic absorption spectroscopy. The chemical composition of natural zeolite particles useful in the method of the invention can be as follows:

$SiO_2$: 65.0-71.3%
$Al_2O_3$: 11.5-13.1%
$CaO$: 2.7-5.2%
$K_2O$: 2.2-3.4%
$Fe_2O_3$ 0.7-1.9%
$MgO$: 0.6-1.2%
$Na_2O$: 0.2-1.3%
$TiO_2$: 0.1-0.3%

The natural zeolite particles provided in step (a) should have a particle size ranging between 0.001 and 0.5 mm. If the naturally obtained zeolite particles are larger, they can be mechanically milled once to achieve the desired particle size. Generally, impact mills such as pin or ball mills are used for this mechanical milling.

In a ball mill, size reduction is achieved by impact and attrition. A ball mill consists of a hollow cylindrical shell rotating about its axis. The axis of the shell may be either horizontal or at a small angle to the horizontal. It is partially filled with balls, which form the grinding media and which may be made of steel (chrome steel), stainless steel or rubber. The inner surface of the cylindrical shell is usually lined with an abrasion-resistant material such as manganese steel or rubber. As the shell rotates, the balls are lifted on the rising side of the shell. Subsequently, they cascade down or drop down onto the feed. This results in impact on solid particles which are present between the balls and the inner surface of the shell, which are thus reduced in size.

A pin mill is a mill that comminutes materials by the action of pins that repeatedly move past each other. It breaks up particles through repeated impact between particles and pins. The pin mill is a type of vertical shaft impactor mill. In a vertical shaft impactor mill, particles are primarily micronized due to the impact between the (accelerated) particles and a hard surface inside the mill. A pin mill consists of two rotating disks with pins embedded on one face. Generally, both pin discs are rotated in opposite directions which allows high relative speeds. The disks are arrayed parallel to each other so that the pins of one disk face those of the other. The substance to be milled is fed into the space between the disks and either one or both disks are rotated at high speeds. A pin mill is designed for the dry milling of soft to medium-hard materials and can be used on both dry substances and liquid suspensions.

In the method of the invention, an improved tribo-mechanical micronisation or activation is carried out in a micronization device which micronizes the particles in a particle by particle collision process by accelerating the particles through whirlwinds which are generated by at least three circular rows of blades (4, 5) fixed on two counter-rotating discs (2, 3), wherein the blades protrude into corresponding channels (8) located on the opposing disc, and wherein the counter-rotating discs (2, 3) are arranged such that the particles have to pass all circular rows of blades (4, 5) by centrifugal force.

The treatment of the zeolite particles with a gas containing at least 95 mol-% of oxygen throughout the micronisation steps can be achieved by blowing the gas into the micronization device through a gas feed tube (7) connected to the particle inlet tube (6) of the micronization device.

The tribo-mechanical micronization unit (grinding chamber) of the micronisation device is preferably a round cylindrical working chamber which can be cooled with water. The counter-rotating disks preferably rotate in opposite directions at the same angular rate and are preferably made of stainless steel. The zeolite particles preferably enter the micronization device through the central part of the rotor system by means of a particle inlet tube (6) and a funnel. The input into the activation process can be automatically controlled and can be exactly regulated by e.g. a spiral conveyer. For example, the input of zeolite particles can be regulated at 70 gram per second. Due to the suction effect of the micronization device, the zeolite particles are sucked into the micronization device, upon which they are accelerated through whirlwinds.

The whirlwinds are generated by at least three circular rows of blades (4, 5). Preferably, they are generated by seven circular rows of adjustable blades which are screwed on the counter-rotating discs. The blades are adjustable in that their angle can be adjusted up to 5 degrees by means of a special degree gauge (accuracy of 0.01 degree), which allows the optimization of the blade angle and, as a consequence, of the particle by particle collisions. The adjustment range of the blades (plus/minus 2.5 degrees) is confined by precise surface cuttings in the counter-rotating discs. The blades are fixed via wear-resistant screws by means of a dynamometric key. Additionally, the blades are replaceable. Preferably, the blades are trapezoidal.

The blades protrude into corresponding channels (8) located on the opposing disc. Preferably, only minimal tolerances should be allowed between the blades and the opposing disc. Furthermore, the counter-rotating discs (2, 3) are arranged such that the particles have to pass all circular rows of blades (4, 5) by centrifugal force.

After this procedure, the material falls down into an outlet funnel which is attached to the lower part of the micronization device and the particles can be collected at the outlet port of the device. In case the zeolite particle composition is intended for medical use, a product collection method which is in compliance with pharmaceutical manufacturing requirements is used.

It was found that the physical characteristics such as fracture pattern, particle size and surface character of micronized zeolite particles can be further optimized when the ambient air, which is sucked into the inlet funnel together with the zeolite material, is substituted by a gas containing at least 95 mol-% of oxygen. Preferably, medical grade oxygen is used.

To achieve this, the gas containing at least 95 mol-% of oxygen can be blown into the micronization device through a gas feed tube (7) connected to the particle inlet tube (6) of the micronization device. For example, the gas can be continuously blown in the particle inlet tube (6) through a nozzle or air injector. The air injector accelerates the product through the particle inlet tube and into the cylindrical grinding chamber. Preferably, the amount of the oxygen-containing gas introduced in the micronization device is 1 to 5 liters at 23° C. and 1013.25 hPa per kg of zeolite particles introduced in the device. For example, the amount of oxygen-containing gas introduced in the micronisation device can be 3.6 liters per kg of zeolite particles introduced in the device.

In the micronization device, the particles are exposed to optimized multiple high-speed particle by particle collisions. More particularly, the particles are subjected to a combination of forces. The free vortex created by the jet stream exerts a centrifugal force on the particles and the gas flow through the micronizing area creates an opposing drag force. The particles are accelerated and, because of the repeated change of direction of motion, they are in constant collision, which causes a high degree of friction in short time intervals. Larger particles of greater mass are forced towards the outside of the grinding chamber, whilst finer particles migrate towards the central outlet port and eventually into the product collector. The particle to particle collisions created within the micronizing chamber cause the majority of the size reduction. The centrifugal force inside the mill combined with the different particle sizes allows the classification of the obtained particles into the required size distribution metrics.

The above described micronization process is executed more than once. To this end, the particles collected after the first micronization step are re-introduced in the above described micronization device (the first micronisation device) or introduced in further micronization devices (the second and further micronisation devices). Preferably, the process is executed twice in a first micronisation device or in a first and second micronisation device.

In a preferred embodiment, the particles collected at the outlet port of the first micronisation device are introduced into the first or second micronization device through a particle transporting system which connects the particle outlet port of the first micronization device with the particle inlet tube of the same or further micronization device. In the most preferred embodiment, the zeolite material is after a first tribo-mechanical micronization immediately exposed to a second tribo-mechanical micronization, where the micronization devices are serially linked. The devices can e.g. be connected by a spiral conveyer which transports the particles from the outlet port of the first device to the inlet port of the second device. Thus, the tribo-mechanical micronization process can automatically and immediately be executed two consecutive times. This is particularly advantageous since it allows a higher throughput at higher particle temperatures since the once micronized particles do not have to be collected in an interim storage device between the first and the second micronization process.

It was found that performing the micronization process more than once leads to an increase of the particle temperature and an increase of the particle collisions in the oxygen enriched environment. These factors might have contributed to obtaining the specific and advantageous properties of the new zeolite particle compositions.

The particles can be transported to the first micronisation device by e.g. a spiral conveyer that transports the particles from e.g. a big-bag emptying unit to the inlet port. At the end of the one or more micronisation processes, the particles can be passed through a flow separator. This allows controlling the average particle size and overall particle size distribution. In particular, a flow separator is used to separate larger zeolite particles in order to produce a zeolite powder of higher quality with a smaller average particle size and a more homogeneous particle size distribution.

In specific embodiments, the micronization process can for example be characterized by the following parameters:
 Zeolite particle feed rate: 3 to 4.5 kg/minute
 Flow of the oxygen-containing gas: 12 to 16 liter/minute
 Feed particle size: 0.001 to 0.5 mm
 Velocity of the blades: 125 to 150 m/s In a preferred embodiment, the micronization process can be characterized by the following parameters:
 Zeolite particle feed rate: 4.2 kg/minute
 Flow of the oxygen-containing gas: 15 liter/minute
 Feed particle size: 0.005 to 0.150 mm
 Velocity of the blades: 145 m/s The zeolite particle compositions of the invention can be obtained by the above described methods. The compositions differ from zeolite particle compositions obtainable by other methods by the above described particle characteristics leading to advantageous effects when the particles are used in methods of treating or preventing certain conditions of the human or animal body and when used as food additive, as filter for purification of water, in packaging materials, or as cosmetic ingredient.

Apparatus

The present invention also provides an improved apparatus for the production of a zeolite particle composition.

The apparatus contains at least one micronization device containing a particle inlet tube (6), a gas feed tube (7) connected to the particle inlet tube (6), a tribo-mechanical micronization unit, and a particle outlet port.

The tribo-mechanical micronization unit (grinding chamber) of the micronisation device is preferably a round cylindrical working chamber which can be cooled with water. The micronization device contains two counter-rotating discs which rotate at the same high angular speed in opposite directions. A rotor speed of about 8250 revolutions per minute can be achieved. The discs are preferably made of stainless steel. Each rotating disk is supplied with at least three circular rows of blades (4, 5). Preferably, there are seven circular rows of adjustable blades made of hard metal which are screwed on the counter-rotating discs. The blades are adjustable in that their angle can be adjusted up to 5 degrees by means of a special degree gauge (accuracy of 0.01 degree), which allows the optimization of the blade angles and, as a consequence, of the particle by particle collisions. The adjustment range of the blades (plus/minus 2.5 degrees) is confined by precise surface cuttings in the counter-rotating discs. The blades are fixed via wear-resistant screws by means of a dynamometric key.

Additionally, the blades are replaceable. Preferably, the blades are trapezoidal.

The blades protrude into corresponding channels (8) located on the opposing disc. Preferably, only minimal tolerances should be allowed between the blades and the opposing disc, preventing the material from passing through under the blades. Furthermore, the counter-rotating discs (2, 3) are arranged such that the particles have to pass all circular rows of blades (4, 5) by centrifugal force.

The particle inlet tube (6) is preferably connected to the device such that particles can be introduced into the central part of the rotor system.

Compared with the tribo-mechanical micronization devices known from the prior art (e.g. EP 1 107 826), the apparatus of the present invention has a gas feed tube (7) connected to the particle inlet tube (6). To introduce the gas, a nozzle or air injector can be connected to the micronization device. Connecting the gas feed tube with the particle inlet tube ensures that the oxygen-containing gas is available during the whole activation process.

An outlet funnel which is attached to the lower part of the micronization device allows to collect the micronized particles at the outlet port of the device.

The apparatus preferably contains at least a first and a second micronization device wherein the micronization devices are connected through a particle transporting system which connects the outlet port of the first micronization device with the particle inlet tube of the second micronization device. This is particularly advantageous since it allows a higher throughput at higher particle temperatures since the once micronized particles do not have to be collected in an interim storage device between the first and the second micronization process.

In a specific embodiment, the micronisation devices are characterized by the following dimensions:

Diameter of the particle inlet tube: 19 mm
Diameter of the gas feed tube: 6 mm
Angle between gas feed tube and particle inlet tube: 30 degrees
Diameter of micronizing chamber: 380 mm
Dimensions of the outlet port: 170 mm×20 mm Use of the Zeolite Particle Compositions The invention also provides zeolite particle compositions for use in a method for treatment of the human or animal body by therapy and/or prophylaxis, where the zeolite particle composition is characterized by the above described properties.

More specifically, the zeolite particle composition is characterized by particles having a specific surface area of 30.5 to 30.8 m$^2$/g, wherein the specific surface area is measured by multipoint BET surface area measurement and an average of zeta potential values of less than −12.00 mV, wherein the zeta potential values are measured after addition of Ni$^{2+}$ ions at a concentration of 0.001 M to 50 ml of an aqueous composition containing 50 mg of zeolite particles at different pH values in the pH range of 3.2 to 6.0 where the different pH values are achieved by adding 0.1 M in aliquots of 20 µl to the aqueous composition and wherein the zeta potential values are calculated based upon experimentally-determined electrophoretic mobility.

Preferably, the particles are further characterized by a silicon to aluminum ratio at the surface of 4.0 to 5.5, wherein the ratio is measured by Energy Dispersive X-ray Diffraction at an accelerating voltage of 15 kV.

Also, a zeolite particle composition for use in a method for treatment of the human or animal body by therapy and/or prophylaxis is provided where the zeolite particle composition is characterized by being obtained by the above described novel method of preparing zeolite particle compositions.

Particularly, the invention provides such zeolite particle compositions for use in a method of treating or preventing conditions of the human or animal body, or symptoms of these conditions, that are related to heavy metals, endotoxins, exotoxins, and/or bacterial, viral or parasitic intoxications in or of the digestive system, mucosal surfaces or the skin.

For example, the zeolite particle composition can be used in a method of preventing, reducing or eliminating symptoms associated with a chronic disease or organ malfunction which is caused by exposure to toxic agents, where an effective amount of the zeolite composition is administered before, simultaneously with or after the exposure to toxic agents.

The zeolite particle compositions can be used in conditions selected from the group consisting of diarrhea caused by bacteria, diarrhea caused by viruses, diarrhea caused by parasites, food poisoning, heavy metal poisoning, toxin or drug poisoning, dental plaque, osteoporosis, liver diseases, kidney diseases, autoimmune illnesses, neuropathic pain, macular degeneration, hypercholesterolemia, diabetes mellitus, neurodegenerative disease, parodontitis, neurodermitis, dermatopathies, Crohn's disease, irritable bowel syndrome, cancer metastases and neural regeneration.

Toxic agents are organopoisoning materials and other natural and synthetic toxins, heavy metals, and free radicals produced within the body as a reaction to exogenic causes, aging and stress.

Examples of organopoisoning materials and other natural and synthetic toxins and heavy metals are nicotine, ethanol, methanol, ammonia, Cd, Pb, Zn, Cu, Cr, Ni, Hg, Al, radioactive isotopes of caesium and strontium, anions like chromates, bichromates, arsenites, persistent organic pollutants that include aldrin, dieldrin, endrin, chlordane, heptachlor, DDT, mirex, hexachlorobenzene, toxaphene, polychlorinated biphenyls (PCB), polychlorinated dibenzo p-dioxins (PCDD), polychlorinated dibenzofurans (PCDF), other organochlorine pesticides and other pesticides, mycotoxins including aflatoxins produced primarily by the fungi *Aspergillus flavus* and *Aspergillus parasiticus*, drugs including cytostatics such as for example doxorubicine, 5-fluorouracile, cis-platin and carbo-platin, theophylline, antipsychotics, analgesics, antibiotics such as for example beta-lactams, cephalosporins, glycopeptides, everninomycins, macrolides, streptogramins, chloramphenicol, fusidic acid, tetracyclines, lincosamides, aminoglycosides, oxazolidinones, quinolones, rifamycines, sulfonamides and trimethoprim (TMP), and antifungal azoles and polyenes.

Preferably, the zeolite particle compositions are used in conditions caused by a toxin or drug selected from the group consisting of nicotine, ethanol, methanol, theophylline, antipsychotics, analgesics and antibiotics.

The zeolite particle compositions can be administered to a patient at an oral daily dose of from about 1 to about 500 mg/kg of body weight, and preferably from about 10 to about 250 mg/kg of body weight. The daily dose is administered once per day or two to four times per day by dividing it into two to four portions. The dose can be adjusted depending on the individual patient by taking the symptoms, age, sex, and the like into consideration.

The zeolite particle compositions provided in this invention or obtained by the provided method are particularly efficient in these methods.

Furthermore, the invention provides the use of the zeolite particle compositions as a food additive, as a filter for purification of water, in packaging materials, or as a cosmetic ingredient.

For example, the zeolite particle compositions can be contained in commercial cosmetic products such as creams, which can be used in the cosmetic treatment of skin conditions.

Pharmaceutical Compositions

The invention also provides novel pharmaceutical compositions containing a zeolite particle composition characterized by the above described properties.

More specifically, the zeolite particle composition is characterized by particles having a specific surface area of 30.5 to 30.8 m$^2$/g, wherein the specific surface area is measured by multipoint BET surface area measurement and an average of zeta potential values of less than −12.00 mV, wherein the zeta potential values are measured after addition of Ni$^{2+}$ ions at a concentration of 0.001 M to 50 ml of an aqueous composition containing 50 mg of zeolite particles at different pH values in the pH range of 3.2 to 6.0 where the different pH values are achieved by adding 0.1 M HCl in aliquots of 20 µl to the aqueous composition and wherein the zeta potential values are calculated based upon experimentally-determined electrophoretic mobility. Preferably, the particles are further characterized by a silicon to aluminum ratio at the surface of 4.0 to 5.5, wherein the ratio is measured by Energy Dispersive X-ray Diffraction at an accelerating voltage of 15 kV.

Also, the zeolite particle composition contained in the pharmaceutical compositions can be characterized by being obtained by the above described novel method of preparing zeolite particle compositions.

The pharmaceutical compositions can be used in any of the above described methods of treating or preventing conditions of the human or animal body.

Preferably, the pharmaceutical compositions comprise an effective amount of the zeolite particle composition and a pharmaceutically acceptable carrier.

The pharmaceutical compositions can be provided in a commercial package including the pharmaceutical composition and instructions that the composition is indicated for treating or preventing conditions of the human or animal body, or symptoms of these conditions, that are related to heavy metals, endotoxins, exotoxins, and/or bacterial, viral or parasitic intoxications in or of the digestive system, mucosal surfaces or the skin.

In the pharmaceutical compositions, the zeolite particle composition can be mixed with dolomite. The preferred weight ratio of zeolite particle composition to dolomite is in the range from 7:3 to 9:1.

The pharmaceutical compositions may be for oral administration or external use.

Where intended for oral administration, the compositions can be solid or liquid.

Examples of solid compositions for oral administration are tablets, pills, capsules, powders, granules, or the like. In such a solid composition, one or more active ingredients can be mixed with an inert diluent such as lactose, mannitol, glucose, hydroxypropyl cellulose, microcrystalline cellulose, starch, polyvinylpyrrolidone, and/or magnesium metasilicate aluminate. Preferably, the compositions contain at least one such diluent. The compositions may further contain additives other than the inert diluent, for example lubricants such as magnesium stearate, disintegrating agents such as cellulose calcium glycolate, stabilizing agents, and/or solubilizing agents. Solid compositions in the form of tablets, pills or capsules may be coated with a coating containing for example sucrose, gelatin, hydroxypropyl cellulose, hydroxypropylmethyl cellulose phthalate, or the like, or with a film containing for example a gastric-soluble or enteric-soluble substance, as needed.

Examples of liquid compositions for oral administration include pharmaceutically acceptable suspensions, and the like. Such compositions generally contain a commonly used inert diluent such as purified water or ethanol. The liquid compositions may further contain auxiliary agents such as wetting agents, suspending agents, sweeteners, flavors, perfumes, and/or preservatives.

Examples of useful compositions for external use are ointments, creams, gels, powders and suspensions.

The pharmaceutical compositions can be prepared by commonly known methods which comprise the mixing of the zeolite particle composition with pharmaceutically acceptable excipients.

The present invention is illustrated by the following examples:

Example 1: Preparation of Zeolite Particle Composition According to the Invention Natural zeolite particles containing 86% clinoptilolite, 6% cristobalite, 5% biotite, 2% silica and traces of feldspar, illite and carbonate minerals and having a volume based particle size ranging between 0.005 and 0.150 mm were introduced in a tribo-mechanical micronization unit. The particle inlet tube had a diameter of 19 mm, the diameter of the micronizing chamber was 380 mm and the dimensions of the outlet port were 170 mm×20 mm. The particles were introduced in the micronization unit at a feed rate of 4.2 kg/minute. Together with the particles, an oxygen gas flow was introduced in the micronizing chamber through a gas feed tube having a diameter of 6 mm and which was connected to the particle inlet tube at an angle of 30 degrees.

The oxygen used was a medical grade oxygen (Medical Oxygen, Air Liquide Healthcare), having a minimum of 99.5 Vol.-% $O_2$. The flow rate of the oxygen gas was 15 liter/minute.

In the micronization unit, the zeolite particles were exposed to optimized multiple high-speed particle by particle collisions by accelerating the particles through whirlwinds which were generated by seven circular rows of blades which were fixed on two counter-rotating discs and wherein the counter-rotating discs were arranged such that the particles had to pass all seven circular rows of blades by centrifugal force. The velocity of the blades was 145 m/s.

The above described tribo-mechanical micronization and oxygenation process was automatically and immediately executed two consecutive times. To this end, the particles collected at the outlet port of the first micronisation device were immediately introduced into an identical second micronization device through a spiral conveyor which connected the particle outlet port of the first micronization device with the particle inlet tube of the second micronization device. The same process parameters, including the oxygen gas flow, as applied during the first micronization process were applied in the second micronization process.

At the end of the process, the particles were passed through a flow separator which separated particles larger than 50 μm from the final zeolite powder.

The zeolite particles produced by the above described process are hereinafter referred to as PMAO2.

Example 2: Preparation of Zeolite Particles by Repeated Micronisation without Treatment with an Oxygen-Containing Gas (Comparative Example)

The micronization process as described in Example 1 was repeated without introducing an oxygen gas flow in the micronization chamber.

The zeolite particles produced by this method are hereinafter referred to as PMA.

Example 3: Preparation of Zeolite Particles with a Prior Art Tribo-Mechanical Activation Method (Comparative Example)

The natural zeolite particles described in Example 1 were micronized in a single micronization device as described in Example 1. Thus, the particles were only micronized once and were immediately collected at the outlet port of the first micronization device. An oxygen gas flow was not introduced into the micronization chamber. After micronisation, the particles were passed through a flow separator. The device dimensions and process parameters were identical to those described in Example 1.

The zeolite particles produced by this method are further referred to as TMAZ.

Example 4: Mechanically Activated Zeolite Particles (Comparative Example)

For comparison, natural zeolite particles which were prepared by micronization in a vertical shaft impactor mill were also characterized. The zeolite particles which were used herein as a reference material are known as MANC® and were obtained from Froximun AG, Schlanstedt, Germany (Toxaprevent® Pure). These particles are further referred to as MANC.

Example 5: Zeolite a (Comparative Example)

Zeolite A particles (Zeolithe Pulver 4A, A.+E. Fischer-Chemie, Germany), which are synthetically grown zeolite particles, were used as a further reference material. However, due to its instability in acidic media, Zeolite A is not interesting for clinical applications.

Example 6: Characterisation of the Zeolite Particle Compositions

The specific surface area of the zeolite particles prepared according to the above examples was determined by nitrogen adsorption/desorption isotherm measurements using a Brunauer-Emmett-Teller (BET) analyzer TriStar II 3020 (Micromeritics, Norcross, Ga., USA). The BET specific surface area, $S_{BET}$, was calculated using the adsorption branch in the relative pressure range between 0.05 and 0.30.

The particle size of the zeolite particle compositions was determined by laser light scattering (diffraction) on a Zeta-Plus instrument (Brookhaven). The powder samples of the zeolites were analyzed as liquid suspensions, without addition of surfactants or other dispersing agents. Ultrasonic dispersion was applied to the sample before measurement of the particle size distribution to avoid particle aggregation. Colloidal solutions were prepared by mixing 250 mg of each zeolite particle composition in 250 mL of Milli-Q water to obtain a final concentration of 0.001 g/mL zeolite particles in solution. After dispersion during 5 minutes in an ultrasonic bath, aliquots of 2.4 mL were placed in plastic cuvettes and the particle size distribution was assessed.

The shape and structure of the zeolite particles was assessed by use of field emission scanning electron microscopy (FE-SEM) in combination with EDS (Energy Dispersive X-ray Spectroscopy; secondary electron images) for the analysis of the elements on the surface. A JSM-7800F FE-SEM instrument (JEOL Ltd., Tokyo) was combined with an X-MAX80 Aztec EDS (Oxford instruments). The zeolite particles were put on a sample holder with carbon paste. Accelerating voltages for SEM and EDS were applied at 2 kV (0.5 kV) and 15 kV, respectively. For EDS measurements, five different places were selected to estimate reproducibility.

A zeta potential analyzer (Instrument ZetaPlus, Brookheaven Instrument Corporation, USA) was used for the zeta potential measurements, where the zeta potential is calculated based upon the experimentally-determined electrophoretic mobility.

For evaluating the change of zeta potential upon addition of $Ni^{2+}$ ions, an acid titration without adding $Ni^{2+}$ ions (i.e. in water), as well as a titration after addition of a constant concentration of $Ni^{2+}$ ions was performed. More in detail, the zeta potential was assessed as follows:

An aqueous zeolite particle composition was prepared by suspending 50 mg of zeolite particles in 50 ml of distilled water in a 100 mL vial on a magnetic stirrer. The pH value was determined. Where necessary, the pH value was adjusted to 11 with 1.0 M NaOH. For the Zeolite A colloidal solution, the pH value was 11.5 and pH adjustment was not necessary. Measurement of the zeta potential was performed in a pH range from 11 to 3. To determine the zeta potential at different decreasing pH values, aliquots of 20 µl of a 0.1 M HCl solution were added by titration. Immediately after addition of each aliquot of HCl, the pH of the zeolite particle composition was measured and an aliquot (2.4 mL) was placed in a plastic cuvette for zeta potential and ion mobility measurement.

The titration was repeated after adding $Ni^{2+}$ ions at a concentration of 0.001 M. More specifically, an aqueous zeolite particle composition was prepared by suspending 50 mg of zeolite particles in 50 ml of distilled water in a 100 mL vial on a magnetic stirrer. 0.1 M $Ni^{2+}$ stock solution was added to obtain a concentration of 0.001 M $Ni^{2+}$ in the aqueous composition. The pH value was determined. Where necessary, the pH was adjusted to 11 with 1.0 M NaOH. For the Zeolite A colloidal solution, the pH value was 11.5 and pH adjustment was not necessary. Measurement of zeta potential was performed in the pH range from 11 to 3. To determine the zeta potential at different decreasing pH values, aliquots of 20 µl of a 0.1 M HCl solution were added. After addition of each aliquot of HCl, the pH was immediately measured and an aliquot (2.4 mL) was placed in a plastic cuvette for zeta potential and ion mobility measurement.

The average of the zeta potential values of the aqueous zeolite compositions containing $Ni^{2+}$ ions, where the different zeta potential values were obtained by the above described acid titration, was calculated from the zeta potential values measured in the pH range of 3.2 to 6.0.

To determine the point of zero charge and the surface charge density, mass titration measurement of the zeolite particle compositions was performed in a concentration range from 0 to 20 g/L in NaCl and HCl solution at an ionic strength of 0.0001 mol $dm^{-3}$. The system measurement set-up included a thermal bath at 25° C., a magnetic stirrer, an ultrasonic probe and a gas inlet for argon. After addition of a small amount of zeolite particle composition in solution, the ultrasonic probe was applied for one minute. Measurement of the solution pH value was carried out under argon with a glass electrode. The procedure was repeated for NaCl and HCl until the pH value stabilized and did not change upon addition of a new zeolite particle composition portion.

Figure 6A:
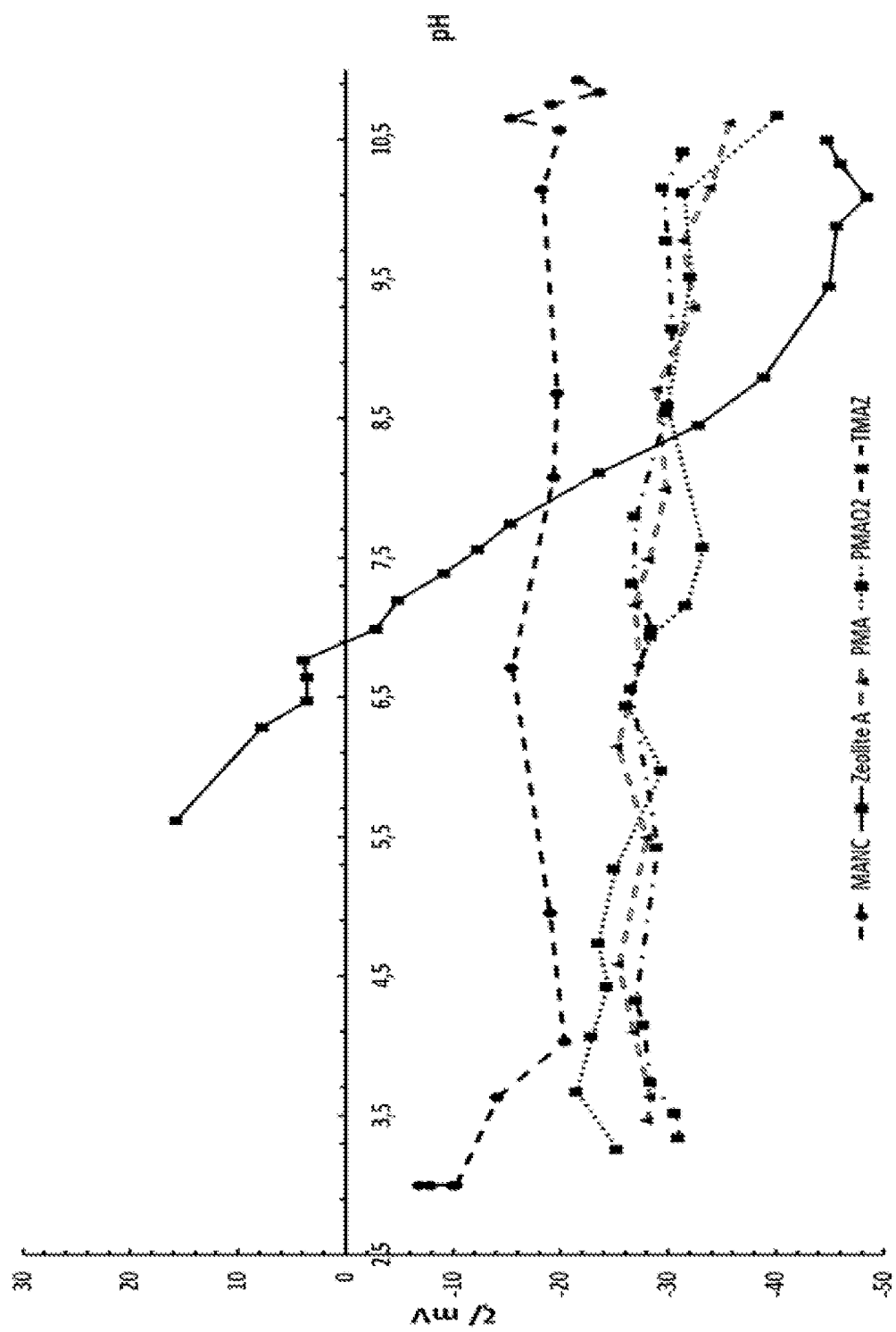
FIG. 6A and FIG. 6B show the zeta potential values of aqueous compositions containing different zeolite particles, without and with $Ni^{2+}$ ions at a concentration of 0.001 M, respectively, measured at different pH values in a pH range of 3 to 10 and calculated based upon experimentally-determined electrophoretic mobility. The figures show the results for zeolite particles according to the invention, obtained as described in Example 1, for particles prepared by repeated tribo-mechnanical micronization without treatment with an oxygen-containing gas, obtained as described in Example 2, for particles subjected to a single tribo-mechanical micronization without oxygen treatment, obtained as described in Example 3, for particles micronized by mechanical activation, described in Example 4, and for Zeolite A particles.
Figure 6B:
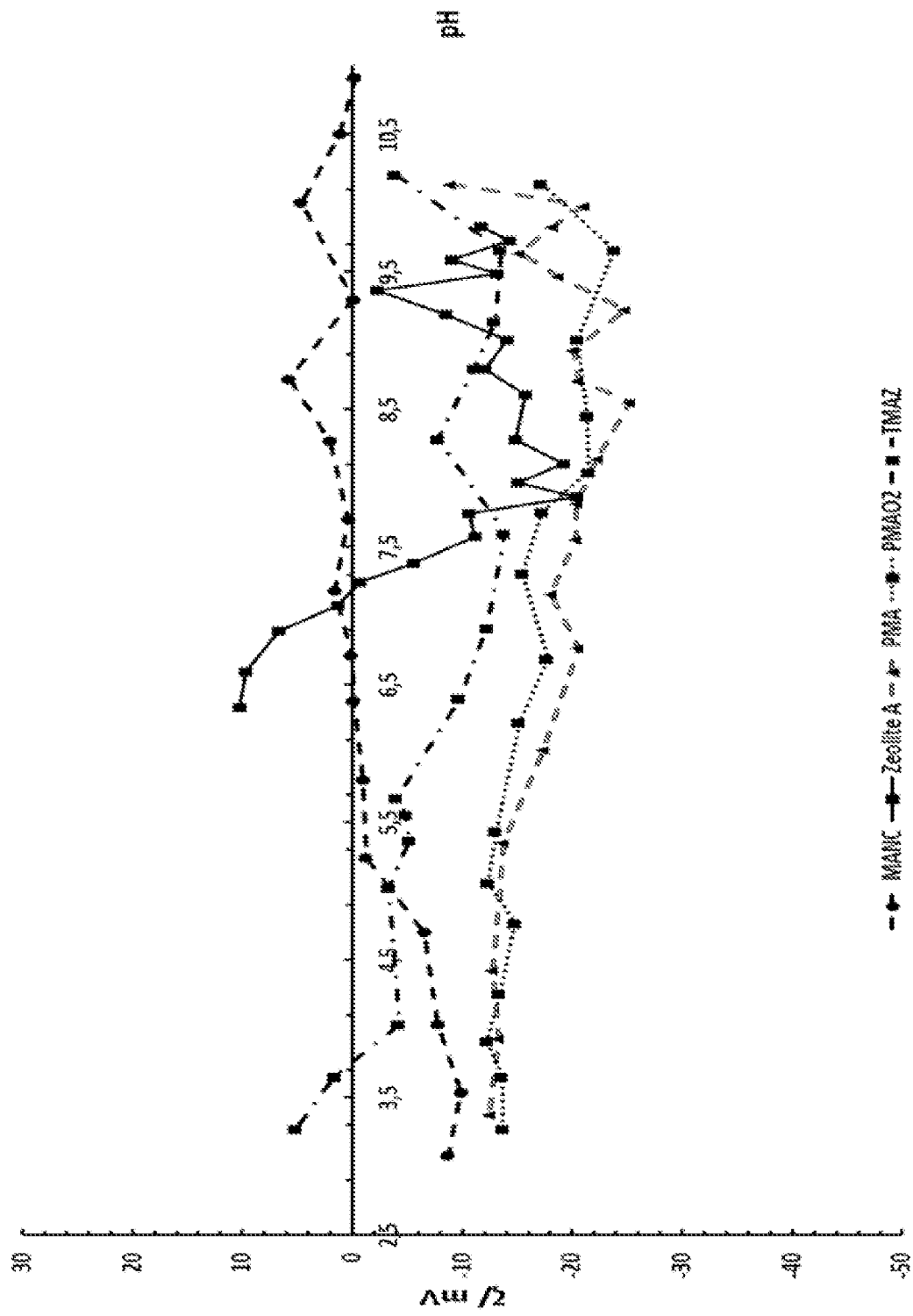

The results of the above described measurements are summarized in Table 1 below. The zeta potential values measured by acid titration in the pH range of 3 to 10 in water and after addition of the constant concentration of $Ni^{2+}$ ions are shown for the different zeolite preparations in FIGS. 6(A) and 6(B).

TABLE 1

Physical and chemical properties of zeolite particle compositions

| | | Minimum | Maximum |
|---|---|---|---|
| Zeolite particle composition according to Example 1 | | | |
| Surface area - measured by multipoint BET method | 30.7 $m^2$/g | −0.5% | +0.5% |
| Standard flake-like structures - measured by FE-SEM | Yes | In all tested samples | In all tested samples |
| Rounded particles - measured by FE-SEM | Yes | In all tested samples | In all tested samples |
| Ratio Al and Si on surface measured by EDS method | 4.9 | N/A | N/A |

TABLE 1-continued

Physical and chemical properties of zeolite particle compositions

|  |  | Minimum | Maximum |
|---|---|---|---|
| Average zeta potential after addition of $Ni^{2+}$ ions calculated based upon experimentally-determined electrophoretic mobility in pH range 3.2 to 6.0 | −13.3 mV | −13.09 mV | −13.69 mV |
| Zeolite particle composition according to Example 2 (comparative example) | | | |
| Surface area - measured by multipoint BET method | 29.4 $m^2/g$ | −0.5% | +0.5% |
| Standard flake-like structures - measured by FES-EM | Yes | In all tested samples | In all tested samples |
| Rounded particles - measured by FE-SEM | No | In all tested samples | In all tested samples |
| Ratio Al and Si on surface measured by EDS method | 5.5 | N/A | N/A |
| Average zeta potential after addition of $Ni^{2+}$ ions calculated based upon experimentally-determined electrophoretic mobility in pH range 3.2 to 6.0 | −13.1 mV | −13.74 mV | −12.46 mV |
| Zeolite particle composition according to Example 3 (comparative example) | | | |
| Surface area - measured by multipoint BET method | 28.7 $m^2/g$ | −0.5% | +0.5% |
| Standard flake-like structures - measured by FE-SEM | Yes | In all tested samples | In all tested samples |
| Rounded particles - measured by FE-SEM | No | In all tested samples | In all tested samples |
| Ratio Al and Si on surface measured by EDS method | 3.5 | N/A | N/A |
| Average zeta potential after addition of $Ni^{2+}$ ions calculated based upon experimentally-determined electrophoretic mobility in pH range 3.2 to 6.0 | −2.1 mV | −4.04 mV | 5.12 mV |
| Zeolite particle composition according to Example 4 (comparative example) | | | |
| Surface area - measured by multipoint BET method | 20.1 $m^2/g$ | −0.5% | +0.5% |
| Standard flake-like structures - measured by FE-SEM | Yes - Almost undistinguishable | In all tested samples | In all tested samples |
| Rounded particles - measured by FE-SEM | No | In all tested samples | In all tested samples |
| Ratio Al and Si on surface measured by EDS method | 4.3 | N/A | N/A |
| Average zeta potential after addition of $Ni^{2+}$ ions calculated based upon experimentally-determined electrophoretic mobility in pH range 3.2 to 6.0 | −5.28 mV | −9.9 mV | −0.98 mV |
| Zeolite particle composition according to Example 5 (comparative example) | | | |
| Surface area - measured by multipoint BET method | 3.2 $m^2/g$ | −0.5% | +0.5% |
| Standard flake-like structures - measured by FE-SEM | No | In all tested samples | In all tested samples |
| Rounded particles - measured by FE-SEM | No | In all tested samples | In all tested samples |
| Ratio Al and Si on surface measured by EDS method | 1 | N/A | N/A |
| Negative zeta potential after addition of $Ni^{2+}$ ions calculated based upon experimentally-determined electrophoretic mobility in pH range 3.2 to 6.0 | A negative zeta potential is acquired only at pH above 7.0 | N/A | N/A |

Example 7: Heavy Metal Removal from Solution by Different Zeolite Materials in Artificial Stomach and Gut Models This study is an in vitro study which records the selective adsorption of pathogenic substances (heavy metals) in an artificial gut model by means of the following zeolite preparations:
 1. Zeolite A (described in Example 5)
 2. PMAO2 (prepared as described in Example 1)
 3. PMA (prepared as described in Example 2)
 4. MANC (described in Example 4)

The experiment was performed in a multi-toxine-solution (as is also found in everyday life in the chyme) in a simulated gastrointestinal environment. The conditions generally applied in literature for such in vitro experiments were applied.

More particularly, in order to simulate the natural gastric and intestinal environment, HCl and NaCl test solutions were prepared, where solutions having a pH of 1.2 were used to simulate the fasting pH in the human stomach and solutions having a pH of 6.5 to simulate the intestinal (gut) environment.

In a first experiment, the stability of zeolites was investigated at the different pH conditions using 2 g zeolite (Zeolite A, PMAO2, PMA and MANC). The changes of pH were measured at different time intervals during a period of 30 minutes.

It was found that Zeolite A significantly increases the pH value of the artificial stomach solution from 1.21 to 5.06 within 30 minutes after incubation. The PMAO2, PMA and MANC zeolites only caused small pH changes after incubation. This means that the pH remains stable under physiological conditions. The increase of the pH value in a Zeolite A suspension is the result of a release of $Al^{3+}$ ions from the zeolite structure to the buffer solution both in the artificial stomach and gut solution. This means that Zeolite A is unstable under physiologic conditions.

TABLE 2

Time evolution of the pH of the artificial stomach solution after the addition of 2 g of different zeolite preparations at room temperature

| | Zeolite A | PMAO2 | PMA | MANC |
|---|---|---|---|---|
| | | Initial conditions | | |
| Time/min | Temperature 20.5° C., initial buffer pH 1.21 pH | Temperature 20.5° C., initial buffer pH 1.21 pH | Temperature 20.5° C., initial buffer pH 1.21 pH | Temperature 20.5° C., initial buffer pH 1.21 pH |
| 0 | 4.05 | 1.55 | 1.29 | 1.62 |
| 10 | 4.81 | 1.50 | 1.43 | 1.53 |
| 20 | 4.98 | 1.51 | 1.52 | 1.52 |
| 30 | 5.06 | 1.51 | 1.52 | 1.52 |

TABLE 3

Time evolution of the pH of the artificial gut solution after the addition of 2 g of different zeolite preparations at room temperature

| | Zeolite A | PMAO2 | PMA | MANC |
|---|---|---|---|---|
| | | Initial condition | | |
| Time/min | Temperature 20.3° C., initial buffer pH 6.52 pH | Temperature 20.3° C., initial buffer pH 6.52 pH | Temperature 20.3° C., initial buffer pH 6.52 pH | Temperature 20.5° C., initial buffer pH 6.52 pH |
| 0 | 8.81 | 7.92 | 7.76 | 7.76 |
| 10 | 9.92 | 8.10 | 8.04 | 8.04 |
| 20 | 10.07 | 8.10 | 8.06 | 8.06 |
| 30 | 10.11 | 8.10 | 8.06 | 8.06 |

The results in Tables 2 and 3 show that Zeolite A is unstable in the gastrointestinal environment due to the significantly increasing pH. In contrast, the pH values of the solutions to which the other zeolites have been added remain stable.

In a further experiment, the adsorption capacity of the four types of zeolite for heavy metals was determined. In the latter study, different dosages of the zeolites (1, 2 and 3 g) were added to the solutions, as well as specific amounts of heavy metals (As, Cr, Ni, Hg, Pb, Cd). The concentration of the heavy metals in the solutions was measured through a spectrometric method (ICP-OES) and a mercury analysis.

The experiment was designed to mimic real in vivo conditions of the intestine and the stomach. In both the stomach model (low pH) and the gut model (higher pH), the zeolites were capable of removing Pb. Lead is generally very well adsorbed.

However, for the other heavy metals, different adsorption properties of the different zeolite preparations were found.

The main significant differences with respect to the different zeolite preparations are summarized in Tables 5 and 6 below, which show results obtained in solutions containing 3 g and 2 g of the zeolite preparations, respectively. The concentration of each element was assessed at the starting point (i.e. at the time of addition of metal standards before treatment with zeolites) and after incubation with different zeolites (i.e. after 4 h incubation at 37° C. and continuous stirring).

TABLE 4

Reduction of heavy metal concentrations in a gut model solution containing 3 g of different zeolite preparations; * indicates statistically significant changes ($p < 0.05$)

| Contaminant | Zeolite preparation | Concentration starting point [in µg/L] | Concentration after 4 h incubation [in µg/L] |
|---|---|---|---|
| As | PMAO2 | 21.0 | <1.0* |
| | PMA | 21.0 | <1.0* |
| | MANC | 22.0 | 7.5* |
| Cr | PMAO2 | 31.0 | 1.2* |
| | PMA | 31.0 | 2.3* |
| | MANC | 30.0 | 11.5* |
| Ni | PMAO2 | 124.0 | 79.0* |
| | MANC | 102.0 | 97.0 |

TABLE 5

Reduction of heavy metal concentrations in a gut model solution containing 2 g of different zeolite preparations; * indicates statistically significant changes ($p < 0.05$)

| Contaminant | Zeolite preparation | Concentration starting point [in µg/L] | Concentration after 4 h incubation [in µg/L] |
|---|---|---|---|
| As | PMAO2 | 39.3 | 5.5* |
| | PMA | 42.3 | 13.7* |
| | MANC | 18.3 | 9.7* |
| Cr | PMAO2 | 58.1 | 2.5* |
| | PMA | 60.8 | 4.8* |
| | MANC | 32.3 | 2.8* |
| Ni | PMAO2 | 51.5 | 37.5* |
| | PMA | 52.9 | 40.1* |
| | MANC | 25.6 | 16.0* |
| Hg | PMAO2 | 62.7 | 49.7* |
| | MANC | 62.5 | 61.3 |

Thus, the study shows the following:
(1) The known property of zeolites to act as detoxification agents in aqueous solution has now also been documented under physiological conditions in an in vitro gastrointestinal model.
(2) The adsorption potential of various zeolites can be summarized as follows:
  (a) Zeolite A generally has very good binding characteristics in the stomach and in the intestinal environment (except at low dosage). However, due to its instability under physiological conditions it is not suitable for human use (disintegration and release of $Al^{3+}$) and was therefore not tested in the adsorption experiment.
  (b) PMAO2 shows better adsorption characteristics compared with PMA and MANC.
  (c) PMA shows better adsorption characteristics than MANC.

(d) MANC still has good binding characteristics in the stomach and intestinal environment. However, compared with activated zeolite (PMAO2 and PMA) the binding capacity is lower.
(e) General remarks:
  (i) The adsorption of pollutants varies depending on the used dosage of zeolites.
  (ii) The adsorption capacities of natural zeolites are generally more effective in the intestinal milieu due to acid-activation.

The obtained results confirm the enhanced properties of activated zeolite particles according to the invention (PMAO2) on the removal of heavy metals from the gut.

The invention claimed is:

1. A method for the production of a zeolite particle composition, comprising the steps of
  (a) providing natural zeolite particles containing at least 85 wt. % of clinoptilolite as determined by X-ray diffraction and having a volume based particle size as measured by laser diffraction ranging between 0.001 and 0.5 mm;
  (b) introducing the particles provided in step (a) in a first micronization device via a particle inlet tube and tribo-mechanically micronizing the particles;
  (c) collecting the particles micronized in step (b) at a particle outlet port of the first micronization device;
  (d) introducing the particles collected in step (c) in the first or a second micronization device via a particle inlet tube and tribo-mechanically micronizing the particles; and
  (e) collecting the particles micronized in step (d) at a particle outlet port of the second micronization device;
  (f) optionally repeating steps (d) and (e);
  wherein the particles are treated with a gas containing at least 95 mol -% of oxygen throughout at least one of steps (b) or (d).

2. The method of claim 1, wherein the steps of tribo-mechanically micronizing the particles are carried out by micronizing the particles in a particle-by-particle collision process by accelerating the particles through whirlwinds which are generated by at least three circular rows of blades fixed on two counter-rotating discs, wherein the blades protrude into corresponding channels located on the opposing disc, and wherein the counter-rotating discs are arranged such that the particles have to pass all circular rows of blades by centrifugal force.

3. The method of claim 1 or 2, wherein the particles are treated with a gas containing at least 95 mol -% of oxygen throughout at least one of steps (b) or (d) by blowing the gas into the first and/or second micronization device through a gas feed tube connected to the particle inlet tube of the micronization device.

4. The method of claims 1 or 2, wherein the amount of the oxygen-containing gas introduced in the first and/or second micronization device is 1 to 5 liters at 23° C. and 1013.25 hPa per kg of zeolite particles introduced in the device.

5. The method of claims 1 or 2, wherein the particles collected in step (c) are introduced into the first or second micronization device in step (d) through a particle transporting system which connects the particle outlet port of the first micronization device with the particle inlet tube of the first or second micronization device.

* * * * *